United States Patent
Roeloffs

(10) Patent No.: US 10,973,403 B1
(45) Date of Patent: Apr. 13, 2021

(54) HINGE CONSTRUCTION FOR HINGABLY CONNECTING DEVICE MEMBERS TO ONE ANOTHER, IN PARTICULAR FOR A SPECULUM

(71) Applicant: Bridea IP Limited, Hong Kong (CN)

(72) Inventor: Bob Roeloffs, Amsterdam (NL)

(73) Assignee: Bridea IP Limited, Hong Kong (CN)

( * ) Notice: Subject to any disclaimer, the term of this patent is extended or adjusted under 35 U.S.C. 154(b) by 498 days.

(21) Appl. No.: 16/074,127

(22) PCT Filed: Jan. 31, 2017

(86) PCT No.: PCT/NL2017/050059
§ 371 (c)(1),
(2) Date: Jul. 31, 2018

(87) PCT Pub. No.: WO2017/135813
PCT Pub. Date: Aug. 10, 2017

(30) Foreign Application Priority Data

Feb. 3, 2016 (NL) ...................................... 2016213

(51) Int. Cl.
*A61B 1/32* (2006.01)
*F16C 11/04* (2006.01)
(52) U.S. Cl.
CPC ................ *A61B 1/32* (2013.01); *F16C 11/04* (2013.01)
(58) Field of Classification Search
CPC ....... A61B 1/32; A61B 17/02; A61B 17/0218; B25G 3/38; F16C 11/04; Y10T 16/52; Y10T 16/53; Y10T 16/54; Y10T 16/55
See application file for complete search history.

(56) References Cited

U.S. PATENT DOCUMENTS

| 498,633 | A | 5/1893 | Dickinson, Jr. |
| 2006/0122463 | A1 | 6/2006 | Klaassen |
| 2007/0255110 | A1 | 11/2007 | Wax et al. |
| 2010/0217072 | A1 | 8/2010 | Kondoh et al. |
| 2012/0102677 | A1 | 5/2012 | Koarai et al. |

FOREIGN PATENT DOCUMENTS

| CN | 102525392 A | 7/2012 |
| EP | 0655360 A1 | 5/1995 |

*Primary Examiner* — Larry E Waggle, Jr.
(74) *Attorney, Agent, or Firm* — Hoffmann & Baron, LLP

(57) ABSTRACT

A hinge construction hingably connects a first member and a second member which are rotatable about an axis of rotation having an axial direction. A first bearing structure comprises first and second support structures having cylinder surface segment shaped first and second bearing surfaces at a radial distance from the axis of rotation, and configured to slidingly engage each other. Second and third bearing structures comprise third, fourth, fifth and sixth support structures having third, fourth, fifth and sixth bearing surfaces, the third and fourth bearing surfaces, and the fifth and sixth bearing surfaces configured to slidingly engage each other to absorb a force having a force component in the axial direction. A fourth bearing structure comprises seventh and eighth support structures having cylinder surface segment shaped seventh and eighth bearing surfaces at a radial distance from the axis of rotation, and configured to slidingly engage each other.

26 Claims, 12 Drawing Sheets

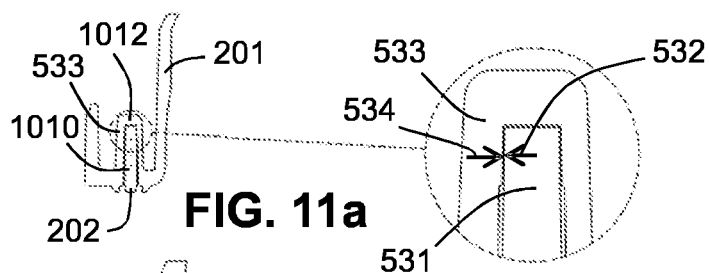
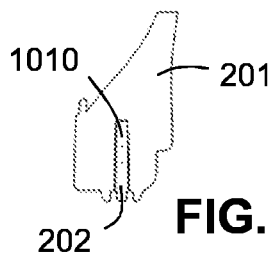
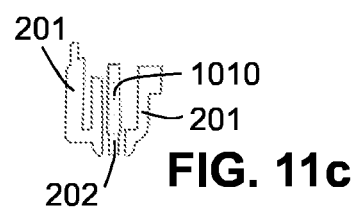
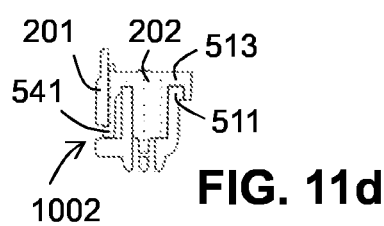
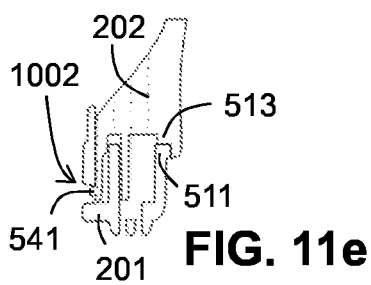
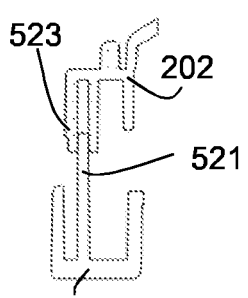
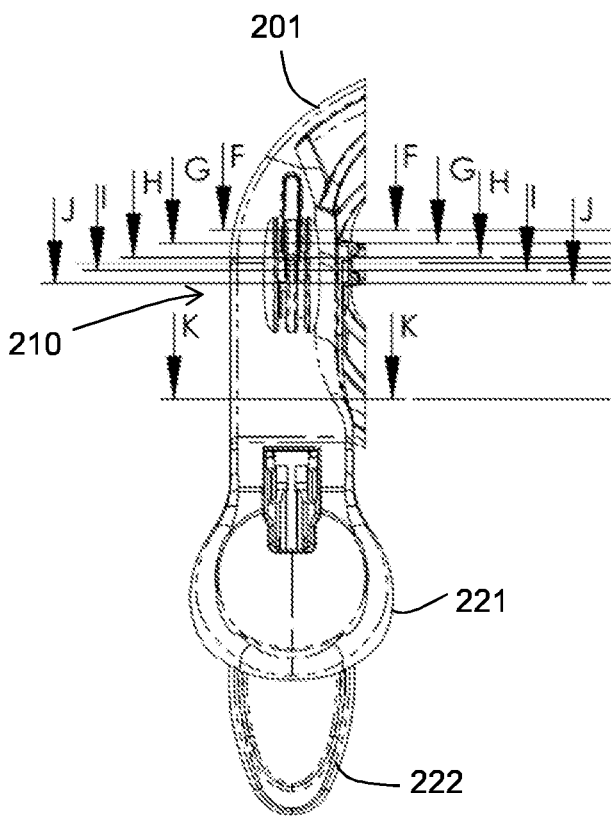

US 10,973,403 B1

HINGE CONSTRUCTION FOR HINGABLY CONNECTING DEVICE MEMBERS TO ONE ANOTHER, IN PARTICULAR FOR A SPECULUM

CROSS-REFERENCE TO RELATED APPLICATIONS

This application is the National Stage of International Application No. PCT/NL2017/050059, filed Jan. 31, 2017, which claims the benefit of Netherlands Application No. NL 2016213, filed Feb. 3, 2016, the contents of which is incorporated by reference herein.

FIELD OF THE INVENTION

The invention relates to the field of hinge constructions for hingably connecting device members to one another, and more specifically to a hinge construction adapted for a speculum, for hingably connecting speculum members to one another.

BACKGROUND OF THE INVENTION

In some hinge constructions whereby two members of a device are hingably connected for rotation around an axis of rotation, having an axial direction, over an angle of less than 360° relative to each other, the hinge construction may be subjected to forces acting on each one of the device members in a plane through the axis of rotation towards the axis of rotation or away from the axis of rotation at an angle to the axial direction, having a force component along a line at right angles to the axial direction. Herein, such forces will be referred to by the expression axilateral forces.

As an example, axilateral forces are generated in a specific type of speculum, which sometimes is referred to as an open-sided speculum such as a Collin or Collins type of speculum.

In such a type of speculum, two elongated beaks members ("duckbilled" members) which are adapted to be inserted into a body cavity, e.g. a vagina, are movable relative to each other to open the body cavity, to provide a passage for visual contact with internal organs and for inserting instruments to perform operations on internal organs. The beak members open and close, i.e. move away from each other and move towards one another, respectively, by rotating the beak members relative to one another using a hinge construction which is positioned one-sided, laterally offset relative to the beak members. This Collins type of speculum provides an advantage of reduced or no interference of the hinge construction of the speculum with any instrument used in the passage provided by the speculum, in particular when compared to other types of hinge constructions.

However, the laterally positioned hinge construction is loaded by axilateral forces when the speculum is used, under pressure of body tissues when the beak members are opened. This poses several requirements on the hinge construction, in particular when the speculum including the hinge construction is manufactured from a moldable material such as a plastic material. The hinge construction must be sufficiently strong to support the beak members not to tilt sideways under load. Furthermore, the hinge construction must not break due to local tension exceeding material limits. Also, the hinge construction must provide low-friction and unobstructed rotation of the beak members under load.

Several different hinge constructions including one-sided laterally offset hinge constructions are known in the art.

Reference US 498633 discloses a speculum having an upper section and a lower section. The upper section at one side is provided with a socket which has produced in it an opening. The lower section is likewise provided with a socket having an opening, which extends through it from top to bottom. A mechanism for manipulating the upper section and lower section has an upper bar and a lower bar, connected by a hinge. The upper bar is adjustably connectable to the upper section by moving it through the opening thereof, and the lower bar is adjustably connectable to the lower section by moving it through the opening thereof.

Reference US 2007/0255110 A1 discloses a speculum including a first structure, which includes a fixed blade member, a second structure, which includes a movable blade member, and a third structure to join the first and second structures together. The speculum includes a hinge, which may be located on either side of the speculum.

The hinge constructions proposed in said references lack stability, and involve a risk of breaking under load in use conditions. Failure during use may injure a patient under examination, and/or the examining medical person.

Thus, a need exists in the field to provide a strong, and stable low-friction hinge mechanism allowing a one-sided laterally offset position relative to the device members that are connected by the hinge mechanism. Furthermore, a need exists to provide such a hinge mechanism suitable to be molded in plastic or metal. In view of injection molding, a need exists to avoid large material wall thickness variations, which would adversely affect the injection molding process, shrinkage, warping, cooling time, material usage and costs. Furthermore, a need exists to avoid overly complex molding tool designs, negative draft angles, undercuts, etc. Also, a need exists to reduce the overall hinge size to avoid excess material usage and a large cumbersome hinge construction design that could obstruct or interfere with the intended use.

Furthermore, when applying such a hinge mechanism in a speculum, a need exists to manufacture the hinge mechanism at low costs and to allow an easy assembly of speculum members, so as to provide a disposable speculum.

SUMMARY OF THE INVENTION

It would be desirable to provide a hinge mechanism that would fulfill at least one of the above needs. It would also be desirable to provide at least an improved hinge mechanism. Furthermore, it would be desirable to provide a hinge mechanism suitable for an open-sided speculum.

To better address one or more of these concerns, in a first aspect of the invention a hinge construction for hingably connecting a first member to a second member is provided, wherein the first member and the second member are rotatable relative to each other about an axis of rotation having an axial direction. The hinge construction comprises:

a first bearing structure comprising a first support structure having a cylinder surface segment shaped first bearing surface at a radial distance from the axis of rotation, and a second support structure having a cylinder surface segment shaped second bearing surface at a radial distance from the axis of rotation, and configured to slidingly engage the first bearing surface, wherein the first support structure is fixed to the first member and the second support structure is fixed to the second member;

a second bearing structure comprising a third support structure having a third bearing surface, and a fourth support structure having a fourth bearing surface, wherein the third bearing surface and the fourth bearing surface are configured to slidingly engage each other to absorb a force having a force component in the axial direction, wherein the third support structure is fixed to the first member and the fourth support structure is fixed to the second member; and a third bearing structure comprising a fifth support structure having a fifth bearing surface, and an sixth support structure having a sixth bearing surface, wherein the fifth bearing surface and the sixth bearing surface are configured to slidingly engage each other to absorb a force having a force component in the axial direction, wherein the fifth support structure is fixed to the second member and the sixth support structure is fixed to the first member.

The hinge construction according to the present invention allows to hingably connect a first member and a second member while being able to absorb substantial axilateral forces in a light-weight and stable hinge structure. The first member and the second member may be rotatable relative to each other over an angle of at most 180°, in particular at most 90°, and more in particular at most 45°. The hinge construction according to the present invention allows a physical implementation which extends over less than 360°, in particular over less than 180° with respect to the axis of rotation.

In particular when the second and third bearing structures have their bearing surfaces at relatively large distances from the axis of rotation and/or at relatively large distances from each other, they have an ability to absorb relatively high axilateral forces, in particular relatively high moments acting in a plane through, or parallel to, the axis of rotation. In case the bearing surfaces of the second and third bearing structures are at relatively small distances from the axis of rotation and/or the hinge construction needs to be stable under relatively large forces acting on it, in an embodiment the hinge construction further comprises a fourth bearing structure comprising a seventh support structure having a cylinder surface segment shaped seventh bearing surface at a radial distance from the axis of rotation, and a eighth support structure having a cylinder surface segment shaped eighth bearing surface at a radial distance from the axis of rotation, and configured to slidingly engage the seventh bearing surface, wherein the seventh support structure is fixed to the second member and the eighth support structure is fixed to the first member. For a high axilateral force absorption capability, it is advantageous to arrange the first bearing structure and the fourth bearing structure at a relatively large distance from each other.

The first, second, seventh and eighth bearing surfaces are cylinder surface segment shaped, and therefore each extend over a part of a circumference, so less than 360°, of the (imaginary full) cylinder surface, and in some embodiments one or more of these bearing surfaces extend over less than 180°. The first, second, seventh and eighth bearing surfaces, and also the corresponding first, second, seventh and eighth support structures, thereby occupy a limited space (volume), and a limited area in a tangential and axial direction which nevertheless can be designed to safely absorb radial forces exerted on the first and fourth bearing structures by axilateral forces acting between the first member and the second member in any designed angular position of the first member and the second member relative to each other, wherein the first and second bearing surfaces at least partially overlap in their sliding engagement, and wherein the seventh and eighth bearing surfaces at least partially overlap in their sliding engagement. Thus, the hinge construction can be relatively small, and may require a relatively low amount of material.

The design of the first, second, third, fourth, fifth, sixth, seventh, eighth (and possible more) bearing surfaces may be determined by the actual maximum angle of rotation of the first member and the second member relative to each other, and by the shape of the bearing surfaces, i.e. point or multi-point shaped, line or multi-line shaped, or surface area shaped.

In an embodiment of the hinge construction, one of the first and second bearing surfaces is convex and the other one of the first and second bearing surfaces is concave, and one of the seventh and eighth bearing surfaces is convex and the other one of the seventh and eighth bearing surfaces is concave. Thus, the hinge construction allows the first bearing surface to be convex and the second bearing surface, as a consequence, to be concave, while the seventh bearing surface may be either convex or concave and the eighth bearing surface as a consequence being either concave or convex, respectively. Also, the hinge construction allows the first bearing surface to be concave and the second bearing surface, as a consequence, to be convex, while the seventh bearing surface may be either convex or concave and the eighth bearing surface as a consequence being either concave or convex, respectively. Advantageously, both the first bearing surface and the seventh bearing surface are convex, or both the first bearing surface and the seventy bearing surface are concave, which allows for relatively small dimensions of the hinge construction.

Preferably, the first and seventh bearing surfaces are convex and the second and eighth bearing surfaces are concave. This allows for hinge constructions wherein the axis of rotation, which may be virtual, is situated outside the device comprising the hinge construction, which can be advantageous in particular hinge constructions, such as hinge constructions which connect (duck-billed) first and second members of a speculum, for example, where these members provide a greater passage between them at the same angle between the members when compared to an axis of rotation which is inside the device comprising the hinge construction.

The third bearing surface and the fourth bearing surface, as well as the fifth bearing surface and the sixth bearing surface, are configured to slidingly engage each other to absorb a force having a force component in the axial direction, in particular in the same axial direction of the hinge construction. The third, fourth, fifth and sixth bearing surfaces may be shaped in different ways, as long as the third and fourth bearing surfaces, and the fifth and sixth bearing surfaces, respectively, have a continuous contact with each other during rotation of the first member and the second member relative to each other. The contact may be a circle segment shaped line or lines contact, where the line or lines is/are part of the bearing surface. The contact may also be an area contact having radial and tangential dimensions, where the area is part of the bearing surface. The contact may also be a series of point contacts, where the points are located along a circle segment shaped line, or along an area having radial and tangential dimensions. Each one of the third bearing surface, fourth bearing surface, fifth bearing surface and sixth bearing surface may be different from at least one of the other ones, or be the same as the other ones, to establish the point, line(s) or area contact.

The third, fourth, fifth and sixth bearing surfaces may occupy a limited space (volume), and a limited area in a tangential and radial direction which nevertheless can be designed to safely absorb axilateral forces (moments) exerted on the second and third bearing structures by axilateral forces acting between the first member and the second member in any designed angular position of the first member and the second member relative to each other, wherein the third and fourth bearing surfaces at least partially overlap in their sliding engagement, and wherein the fifth and sixth bearing surfaces at least partially overlap in their sliding engagement.

In an embodiment of the hinge construction, at least one of the third, fourth, fifth and sixth bearing surfaces is smooth. Examples of smooth bearing surfaces are smooth curved or double curved surface, a conical surface, (part of) a doughnut-shaped surface, etc.

Smooth bearing surfaces are relatively easy to form, in particular in a moulding process, and provide for a mutual mechanical contact with relatively low local bearing surface pressure, thus reducing friction and risk of breaking of the bearing structure.

In an embodiment of the hinge construction, at least one of the third, fourth, fifth and sixth bearing surfaces is ring segment shaped.

The angular extension of the ring segment may be similar to an angular extension of the cylinder surface segment of any of the first, second, seventh and eighth bearing surfaces.

In an embodiment of the hinge construction, at least one of the third, fourth, fifth and sixth bearing surfaces extends substantially at right angles to the axial direction.

Such extension of at least one of the third, fourth, fifth and sixth bearing surfaces is relatively easy to form, in particular in a moulding process.

In an embodiment of the hinge construction, the first and second bearing surfaces have a first radius with respect to said axis of rotation, and the third and fourth bearing surfaces and/or the fifth and sixth bearing surfaces are positioned away from the axis of rotation at a distance greater than the first radius.

Each one of the third, fourth, fifth and sixth bearing surfaces, as projected on a plane at right angles to the axis of rotation, may have a radial extension relative to the axis of rotation. The smallest radial distance of the radial extension of each one of the third, fourth, fifth and sixth bearing surfaces from the axis of rotation may be greater than the first radius, for the hinge construction to absorb axilateral forces effectively, and to be rigid and strong under axilateral load.

In an embodiment of the hinge construction, the seventh and eighth bearing surfaces have a second radius with respect to said axis of rotation, and the third and fourth and/or the fifth and sixth bearing surfaces are positioned away from the axis of rotation at a distance greater than the second radius.

Each one of the third, fourth, fifth and sixth bearing surfaces, as projected on a plane at right angles to the axis of rotation, may have a radial extension relative to the axis of rotation. The smallest radial distance of the radial extension of each one of the third, fourth, fifth and sixth bearing surfaces from the axis of rotation may be greater than the second radius, for the hinge construction to absorb axilateral forces effectively, and to be rigid and strong under axilateral load. The second radius may be equal to, or different from the first radius.

In an embodiment of the hinge construction, the third bearing surface and the fifth bearing surface face in the same axial direction. Additionally or alternatively, the fourth bearing surface and the sixth bearing surface face in the same axial direction, which may be opposite to the direction in which the third bearing surface and the fifth bearing surface are facing.

The third bearing surface is part of the third support structure fixed to the first member, and the fifth bearing surface is part of the fifth support structure fixed to the second member. When the third bearing surface and the fifth bearing surface face in the same direction, a first axilateral force acting on the first member, and a substantially oppositely acting second axilateral force on the second member, as occur in practice, can be well absorbed.

Similarly, the fourth bearing surface is part of the fourth support structure fixed to the second member, and the sixth bearing surface is part of the sixth support structure fixed to the first member. When the fourth bearing surface and the sixth bearing surface face in the same direction, a first axilateral force acting on the first member, and a substantially oppositely acting second axilateral force on the second member, as occur in practice, can be well absorbed.

It is to be noted here that the greater the distance between the second bearing structure and the third bearing structure, as seen in a radial direction and/or in an axial direction, the more effective they may be in absorbing axilateral forces.

In an embodiment of the hinge construction, the first bearing surface and the eighth bearing surface, in their tangential direction as seen in the axial direction, at most partly overlap. In some embodiments, there may be no overlap. Similarly, the second bearing surface and the seventh bearing surface, in their tangential direction as seen in the axial direction, at most partly overlap. In some embodiments, there may be no overlap.

The first and eighth bearing surfaces both are fixed to the first member, and therefore are fixed relative to each other. The second and seventh bearing surfaces both are fixed to the second member, and therefore are fixed to each other. With a proper selection of the tangential orientation of the first and eighth bearing surfaces, and of the tangential orientation of the second and seventh bearing surfaces, the hinge construction can optimally resist the axilateral forces.

In an embodiment of the hinge construction, the third bearing surface and sixth bearing surface, in their tangential direction as seen from the axial direction, at most partly overlap. In some embodiments, there may be no overlap. Similarly, the fourth bearing surface and fifth bearing surface, in their tangential direction as seen from the axial direction, at most partly overlap. In some embodiments, there may be no overlap.

The third and sixth bearing surfaces both are fixed to the first member, and therefore are fixed relative to each other. The fourth and fifth bearing surfaces both are fixed to the second member, and therefore are fixed to each other. With a proper selection of the tangential orientation of the third and sixth bearing surfaces, and of the tangential orientation of the fourth and fifth bearing surfaces, the hinge construction can optimally resist the axilateral forces. Again, it is noted that the greater the distance between the second bearing structure comprising the third and fourth bearing surfaces, and the third bearing structure comprising the fifth and sixth bearing surfaces, as seen in a radial direction and/or in an axial direction, the more effective they may be in absorbing axilateral forces.

In an embodiment of the hinge construction, the sum of the angular extension of the third bearing surface and the angular extension of the sixth bearing surface is lower than 180°, and/or the sum of the angular extension of the fourth bearing surface and the angular extension of the fifth bearing surface is lower than 180°. With a proper selection of the tangential orientation of the third and sixth bearing surfaces, and of the tangential orientation of the fourth and fifth bearing surfaces, the hinge construction can thus be dimensioned with a minimum of material, while at the same time being sufficiently strong to resist the acting axilateral forces.

In an embodiment of the hinge construction, one of the third support structure and the fourth support structure is substantially fin-shaped and/or one of the fifth support structure and the sixth support structure is substantially fin-shaped. Here, the indication fin-shaped is to be taken as the structure having a tapering shape, wherein one of the sides of the structure is a bearing surface. The fin shape provides sufficient strength and a low material volume.

In an embodiment of the hinge construction, the first and fourth bearing structures are spaced in the axial direction. In a further embodiment, the first, second, third and fourth bearing structures are spaced in the axial direction. Spacing the bearing structures leads to a higher capability to absorb mechanical moments generated by the axilateral forces exerted on the hinge mechanism.

Although in principle an arrangement of the different bearing structures may be arbitrary, as seen along the axis of rotation, in an embodiment of the hinge construction the second and third bearing structures axially are located between the first and fourth bearing structures. In some embodiments of the hinge construction, as seen in the axial direction, the bearing structures are arranged in a sequence of first bearing structure, third bearing structure, second bearing structure, and fourth bearing structure. In such arrangements of the bearing structures, a high capability to absorb mechanical moments generated by the axilateral forces exerted on the hinge mechanism in a relatively small space/volume can be reached.

In an embodiment, the hinge construction further comprises a radial locking structure, comprising a first locking structure and a second locking structure. The radial locking structure may ensure the integrity of the hinge construction, preventing the first member and second member to be movable away from each other, which may otherwise occur for reason of the segment shaped support structures of the hinge construction.

The first locking structure is fixed to the first member, and comprises a first locking surface facing in the radial direction with respect to the axis of rotation. The second locking structure is fixed to the second member, and comprises a second locking surface configured to engage the first locking surface. A mechanical contact between the first locking surface and the second locking surface may be a point to line contact, a point to surface area contact, a multi-point to line contact, a multi-point to surface area contact, a line to line contact, a line to surface area contact, a multi-line to multi-line contact, a multi-line to surface area contact, or a surface area to surface area contact, and can be selected to fulfil requirements of manufacture, assembly, operability and costs of the hinge mechanism.

In a second aspect of the present invention, a speculum is provided, comprising the hinge construction of the present invention. In the speculum, being a surgical instrument, the first member comprises a first beak member and a first handle securely connected to the first beak member, and wherein the second member comprises a second beak member and a second handle securely connected to the second beak member. In a closed state of the speculum, the first beak member and the second beak member are positioned against each other, and the first handle and the second handle are at a first distance, in particular a first angular distance, from each other. In an open state of the speculum, the first beak member and the second beak member are positioned at a distance, in particular a second angular distance, from each other, and the first handle and the second handle are at a third distance, in particular a third angular distance, from each other. The third distance is lower than the first distance.

In an embodiment of the speculum, the hinge construction extends over a first length section of the axis of rotation, and the first beak member and second beak member extend over a second length section of the axis of rotation, wherein the first length section is adjacent the second length section. In use of such a speculum, when moving the first beak member and the second beak member away from each other to bring the speculum in its open state, and to displace tissues in a body cavity of a human or animal patient, axilateral forces are exerted on the hinge construction.

In an embodiment of the speculum, the first handle and the second handle generally extend from the speculum in the first length section of the axis of rotation.

These and other aspects of the invention will be more readily appreciated as the same becomes better understood by reference to the following detailed description and considered in connection with the accompanying drawings in which like reference symbols designate like parts.

BRIEF DESCRIPTION OF THE DRAWINGS

FIG. 2b depicts a view from the first perspective of the first speculum member of the speculum of FIG. 2a.

FIG. 2c depicts a view from the first perspective of the second speculum member of the speculum of FIG. 2a.

FIG. 3a depicts a view from a second perspective of the assembled speculum of FIG. 2a.

FIG. 9 depicts a view from a seventh perspective of the assembled speculum of FIG. 2a in the closed state of FIG. 4a.

FIG. 10 depicts a back view of the assembled speculum of FIG. 2a in the closed state of FIG. 4a.

FIG. 10a depicts a cross-section along the line A-A through the hinge construction of the assembled speculum of FIG. 2a.

FIG. 10b depicts a cross-section along the line B-B through the hinge construction of the assembled speculum of FIG. 2a.

FIG. 10c depicts a cross-section along the line C-C through the hinge construction of the assembled speculum of FIG. 2a.

FIG. 10d depicts a cross-section along the line D-D through the hinge construction of the assembled speculum of FIG. 2a.

FIG. 10e depicts a cross-section along the line E-E through the hinge construction of the assembled speculum of FIG. 2a.

FIG. 11 depicts a back view of the assembled speculum of FIG. 2a in the closed state of FIG. 4a.

FIG. 11a depicts a cross-section along the line F-F through the hinge construction of the assembled speculum of FIG. 2a.

FIG. 11aa depicts an enlarged view of a detail of the cross-section of FIG. 11a.

FIG. 11b depicts a cross-section along the line G-G through the hinge construction of the assembled speculum of FIG. 2a.

FIG. 11c depicts a cross-section along the line H-H through the hinge construction of the assembled speculum of FIG. 2a.

FIG. 11d depicts a cross-section along the line I-I through the hinge construction of the assembled speculum of FIG. 2a.

FIG. 11e depicts a cross-section along the line J-J through the hinge construction of the assembled speculum of FIG. 2a.

FIG. 11f depicts a cross-section along the line K-K through the hinge construction of the assembled speculum of FIG. 2a.

DETAILED DESCRIPTION OF EMBODIMENTS

Figure 1A:
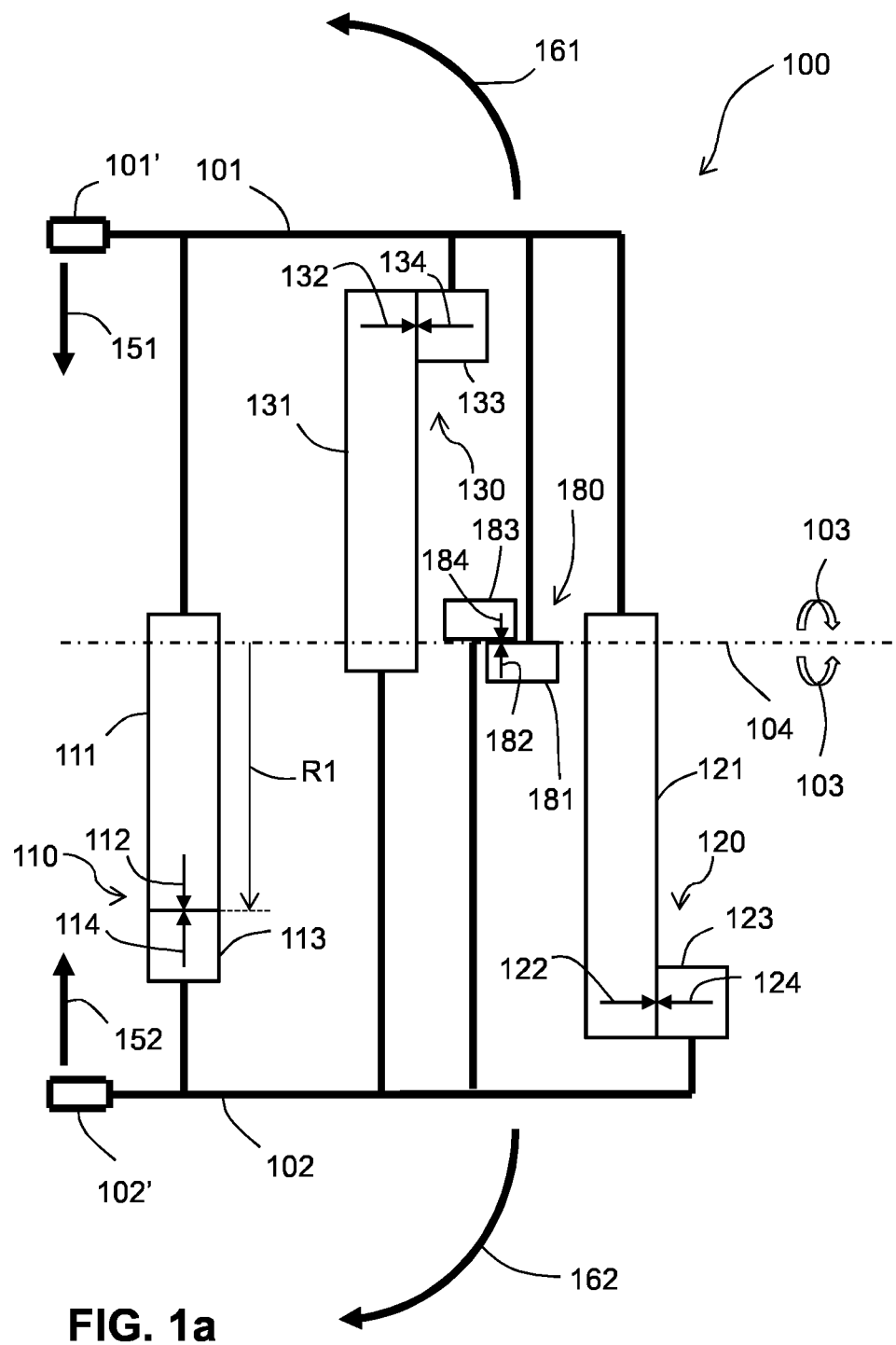
FIG. 1a depicts a schematic diagram of an embodiment of a hinge construction of the present invention, and schematically indicating structures, forces and moments in such a hinge construction.
Figure 1B:
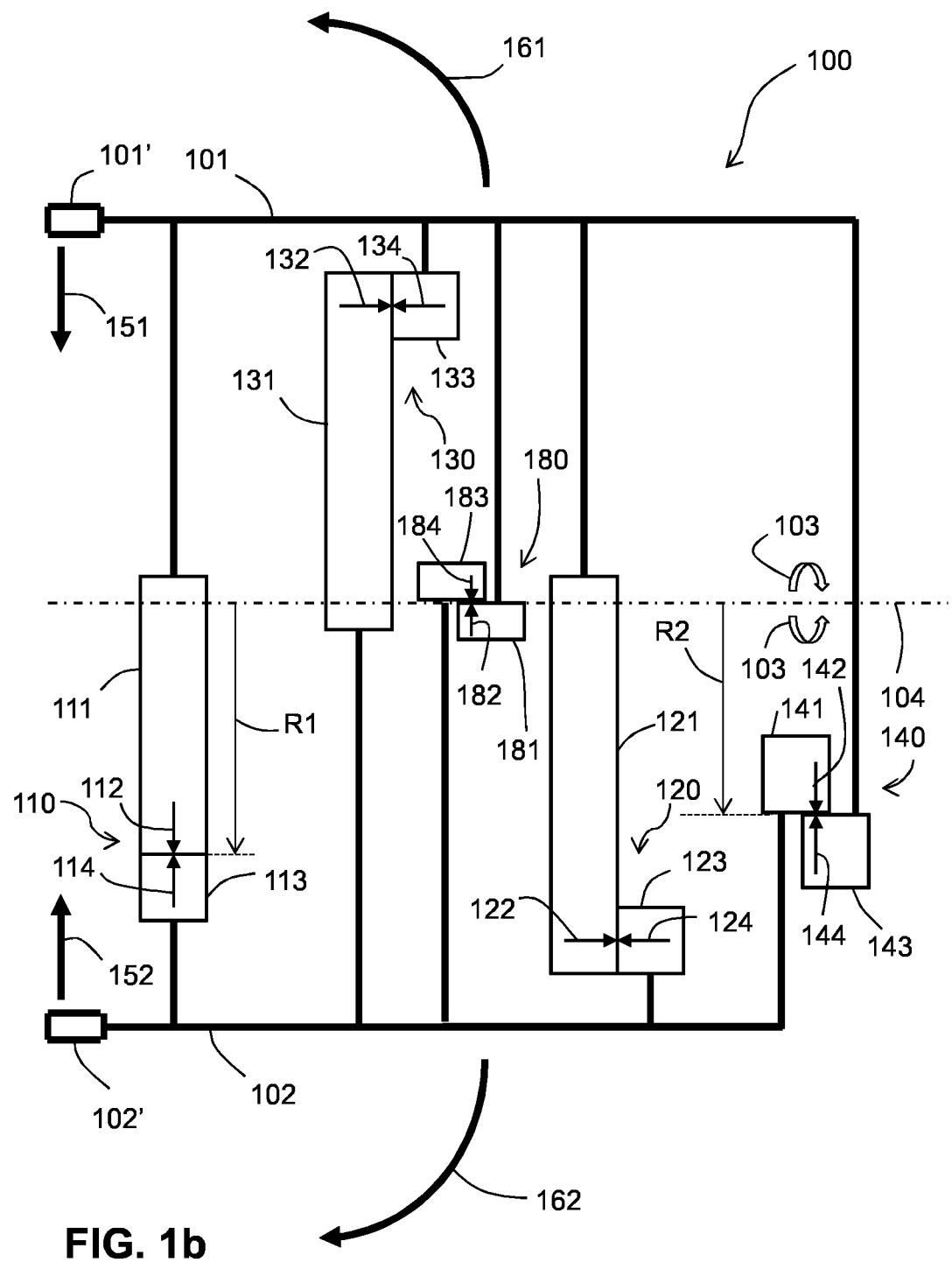
FIG. 1b depicts a schematic diagram of another embodiment of a hinge construction of the present invention, and schematically indicating structures, forces and moments in such a hinge construction.

FIGS. 1a and 1b each depict a schematic diagram of a hinge construction 100, and schematically indicate structures, forces and moments in such a hinge construction 100.

The hinge construction 100 hingably connects a first member 101 to a second member 102. The first member 101 and the second member 102 are indicated by solid lines, and they are rotatable relative to each other, as indicated by double arrows 103, about an axis of rotation 104 having an axial direction. The hinge construction 100, the first member 101 and the second member 102 can take various shapes, depending on an actual product. As an example, below an embodiment of a surgical instrument, in particular a speculum, comprising the hinge construction 100 will be described. However, the hinge construction 100 can be applied in a large variety of products.

The hinge construction 100 comprises a first bearing structure 110, a second bearing structure 120, and a third bearing structure 130 (FIG. 1a), and may further comprise a fourth bearing structure 140 (FIG. 1b), all extending in a tangential direction relative to the axis of rotation 104.

The first bearing structure 110 comprises a first support structure 111 having a cylinder surface segment shaped first bearing surface 112 at a radial distance, first radius, R1 from the axis of rotation 104, and a second support structure 113 having a cylinder surface segment shaped second bearing surface 114 at a radial distance R1 from the axis of rotation 104. The second bearing surface 114 is configured to slidingly engage the first bearing surface 112. The first support structure 111 is fixed to the first member 101, and the second support structure 113 is fixed to the second member 102.

The second bearing structure 120 comprises a third support structure 121 having a third bearing surface 122, and a fourth support structure 123 having a fourth bearing surface 124. The third bearing surface 122 and the fourth bearing surface 124 each extend in a tangential direction, and are configured to slidingly engage each other to absorb a force having a force component in the axial direction. The third support structure 121 is fixed to the first member 101, and the fourth support structure 123 is fixed to the second member 102.

The third bearing structure 130 comprises a fifth support structure 131 having a fifth bearing surface 132, and a sixth support structure 133 having a sixth bearing surface 134. The fifth bearing surface 132 and the sixth bearing surface 134 each extend in a tangential direction, and are configured to slidingly engage each other to absorb a force having a force component in the axial direction. The fifth support structure 131 is fixed to the second member 102, and the sixth support structure 133 is fixed to the first member 101.

The fourth bearing structure 140 comprises a seventh support structure 141 having a cylinder surface segment shaped seventh bearing surface 142 at a radial distance, second radius, R2 from the axis of rotation 104, and an eighth support structure 143 having a cylinder surface segment shaped eighth bearing surface 144 at a radial distance R2 from the axis of rotation 104. The eighth bearing surface 144 is configured to slidingly engage the seventh bearing surface 142. The seventh support structure 141 is fixed to the second member 102, and the eighth support structure 143 is fixed to the first member 101.

The hinge construction 100 extends over a first length section of the axis of rotation 104. Both the first member 101 and the second member 102 comprise a portion 101' and 102', respectively, having a axial position in a second length section of the axis of rotation 104, outside said first length section of the axis of rotation 104. At the portions 101' and 102', the first member 101 and the second member 102, respectively, are subjected to forces acting on the first member 101 and the second member 102 in a plane through, or parallel to, the axis of rotation 104 towards the axis of rotation 104, i.e. having at least force components indicated by arrows 151, 152, respectively, directed at right angles to the axis of rotation 104 in the direction indicated by the arrows. Thereby, the hinge construction 100 is subjected, in the direction indicated by the arrows 151, 152, to moment 161 acting on first member 101, and to moment 162 acting on second member 102.

It is noted that portion 101' of the first member 101 and portion 102' of the second member 102 may alternatively be subjected to forces acting on the first member 101 and the second member 102 in a plane through, or parallel to, the axis of rotation 104 away from the axis of rotation 104, i.e. having at least force components directed at right angles to the axis of rotation 104 in a direction opposite to the direction indicated by the arrows 151, 152. In such circumstances, also the moments acting on the first member 101 and the second member 102 will be oppositely directed to the moments 161, 162.

Herein, the above forces are also referred to as axilateral forces.

In FIGS. 1a and 1b, the first support structure 111, second support structure 113, third support structure 121, fourth support structure 123, fifth support structure 131, sixth support structure 133, seventh support structure 141 and eighth support structure 143 are depicted as rectangular blocks. In practice, however, they can take different forms, e.g. chosen to provide a specific strength, or to provide ease of assembly of the hinge construction 100. Furthermore, in FIG. 1 the first bearing surface 112 and the second bearing surface 114, as well as the third bearing surface 122 and the fourth bearing surface 124, as well as the fifth bearing surface 132 and the sixth bearing surface 134, as well as the seventh bearing surface 142 and the eighth bearing surface 144, are depicted as smooth surfaces contacting each other. In practice, however, the contact may be a point to line contact, a point to surface area contact, a multi-point to line contact, a multi-point to surface area contact, a line to line contact, a line to surface area contact, a multi-line to multi-line contact, a multi-line to surface area contact, or a surface area to surface area contact between the respective bearing surface fixed to the first member 101, and the respective bearing surface fixed to the second member 102. In a practical embodiment, at least one of the third, fourth, fifth and sixth bearing surfaces 122, 124, 132, 134 may be smooth. Furthermore, at least one of the third, fourth, fifth and sixth bearing surfaces 122, 124, 132, 134 may be ring segment shaped, i.e. extend over an angle of less than 360° in a tangential direction. Furthermore, at least one of the third, fourth, fifth and sixth bearing surfaces 122, 124, 132, 134 may extend substantially at right angles to the axial direction. However, the third, fourth, fifth and sixth bearing surfaces 122, 124, 132, 134 may extend at other angles to the axial direction also, as long as they can absorb a force component in the axial direction.

In the hinge constructions 100 of FIGS. 1a and 1b, the third bearing surface 122 and the fifth bearing surface 132 face in the same axial direction (away from the portions 101' and 102', as shown). Similarly, the fourth bearing surface 124 and the sixth bearing surface 134 face in the same axial direction (towards the portions 101' and 102', as shown).

In the hinge construction 100, one of the first bearing surface 112 and second bearing surface 114 is convex, as seen from the axial direction, and the other one of the first bearing surface 112 and second bearing surface 114 is concave. In the embodiment illustrated in FIGS. 1a and 1b, the first bearing surface 112 is convex, and the second bearing surface 114 is concave.

Furthermore, one of the seventh bearing surface 142 and eighth bearing surface 144 is convex, and the other one of the seventh bearing surface 142 and eighth bearing surface 144 is concave. In the embodiment illustrated in FIG. 1b, the seventh bearing surface 142 is convex, and the eighth bearing surface 144 is concave.

The third bearing surface 122 and the fourth bearing surface 124 may be positioned away from the axis of rotation 104 at a distance greater than the first radius R1. Similarly, the fifth bearing surface 132 and the sixth bearing surface 134 may be positioned away from the axis of rotation 104 at a distance greater than the second radius R2. With such arrangements, the moments 161, 162 can be absorbed more effectively than otherwise.

The generally cylinder surface segment shaped first bearing surface 112 and the generally cylinder surface segment shaped eighth bearing surface 144, in their tangential direction as seen from the axial direction, at most partly overlap, to optimally resist axilateral forces.

Similarly, and to obtain a similar effect, the generally cylinder surface segment shaped second bearing surface 114 and the generally cylinder surface segment shaped seventh bearing surface 142, in their tangential direction as seen from the axial direction, at most partly overlap.

Similarly, and to obtain a similar effect, the third bearing surface 122 and the sixth bearing surface 134, in their tangential direction as seen from the axial direction, at most partly overlap. The sum of the angular extension of the third bearing surface 122 and the angular extension of the sixth bearing surface 134 may be lower than 360°, in particular lower than 180°.

Similarly, and to obtain a similar effect, the fourth bearing surface 124 and the fifth bearing surface 132, in their tangential direction as seen from the axial direction, at most partly overlap. The sum of the angular extension of the fourth bearing surface 124 and the angular extension of the fifth bearing surface 132 may be lower than 360°, in particular lower than 180°.

As indicated in FIG. 1b, the first bearing structure 110 and the fourth bearing structure 140 are spaced in the axial direction. In particular, the first bearing structure 110, the second bearing structure 120, the third bearing structure 130 and the fourth bearing structure 140 are spaced in the axial direction, for an optimum absorption of axilateral forces generated by moments 161, 162.

The second bearing structure 120 and the third bearing structure 130 axially are located between the first bearing structure 110 and the fourth bearing structure 140. In particular, as seen in the axial direction from left to right in FIG. 1b, the bearing structures are arranged in a sequence of first bearing structure 110, third bearing structure 130, second bearing structure 120, and fourth bearing structure 140.

As can be seen in FIGS. 1a and 1b, the first member 101 is prevented from moving relative to the second member 102 in the axial direction either to the left or to the right (as seen in FIGS. 1a and 1b), and the second member 102 is prevented from moving relative to the first member 101 in the axial direction either to the left or to the right (as seen in FIGS. 1a and 1b), resulting from the mechanical contact between the third bearing surface 122 and the fourth bearing surface 124, and/or the mechanical contact between the fifth bearing surface 132 and the sixth bearing surface 134.

As can further be seen in FIGS. 1a and 1b, the first member 101 is prevented from moving towards the second member 102 in the radial direction, resulting from the mechanical contact between the first bearing surface 112 and the second bearing surface 114. As can further be seen in FIG. 1b, the first member 101 is prevented from moving away from the second member 102 in the radial direction, resulting from the mechanical contact between the seventh bearing surface 142 and the eighth bearing surface 144.

Further, to prevent the first member 101 from moving away from the second member 102 in a radial direction, a radial locking structure 180 may be provided, which comprises a first locking structure 181 fixed to the first member 101, the first locking structure 181 comprising a first locking surface 182 facing in a radial direction with respect to the axis of rotation 104. The radial locking structure 180 further comprises a second locking structure 183 fixed to the second member 102, the second locking structure 183 comprising a second locking surface 184 configured to engage the first locking surface 182. The first locking surface 182 and the second locking surface 184 are configured to maintain mechanical contact during rotation of the first member 101 and the second member 102 of the hinge construction 100 relative to each other. The mechanical contact between the first locking surface 182 and the second locking surface 184 may be a point to line contact, a point to surface area contact, a multi-point to line contact, a multi-point to surface area contact, a line to line contact, a line to surface area contact, a multi-line to multi-line contact, a multi-line to surface area contact, or a surface area to surface area contact. The first locking surface 182 and the second locking surface 184 may be at a radial distance from the axis of rotation 104. In an embodiment, one of the first locking surface 182 and the second locking surface 184 may be convex, and the other one of the first locking surface 182 and the second locking surface 184 may be concave.

Figure 2A:
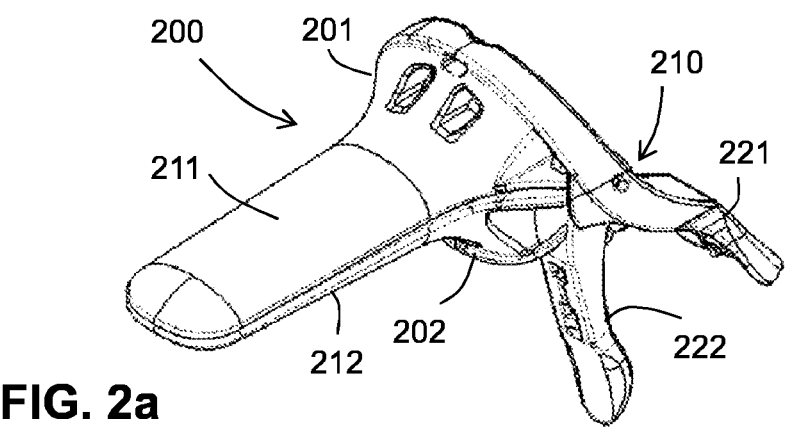
FIG. 2a depicts a view from a first perspective of an assembled speculum, including a first speculum member and a second speculum member connected through a hinge construction in accordance with the present invention.
Figure 2B:
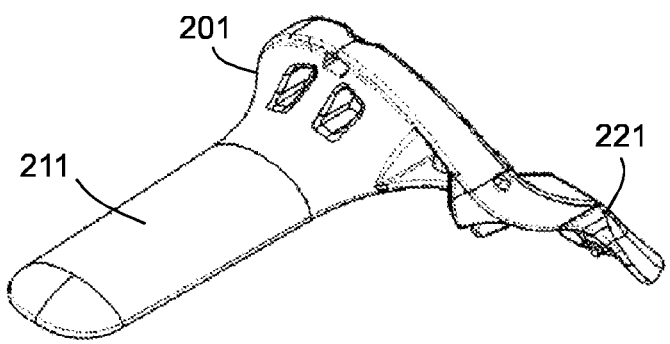
Figure 2C:
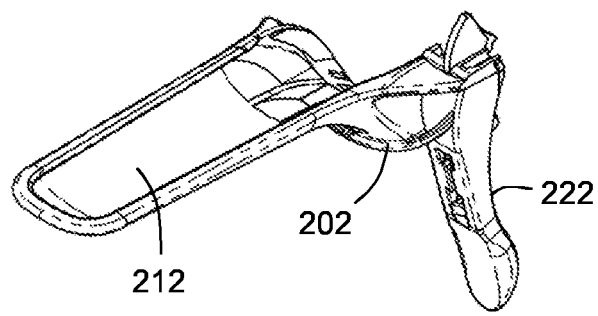

FIG. 2a depicts a view from a first, relatively high perspective of an assembled speculum 200. FIG. 2b depicts a view from the first perspective of a first speculum member 201 of the speculum 200. FIG. 2c depicts a view from the first perspective of a second speculum member 202 of the speculum 200.

The speculum 200 may be manufactured by moulding or forming from a mouldable material, such as a plastic or metal.

The first speculum member 201 comprises a duck-billed first beak member 211, and a first handle 221 fixedly connected to the first beak member 211. The second speculum member 202 comprises a duck-billed second beak member 212, and a second handle 222 fixedly connected to the second beak member 212. The speculum comprises a hinge construction 210 which is explained in further detail below.

Figure 3A:
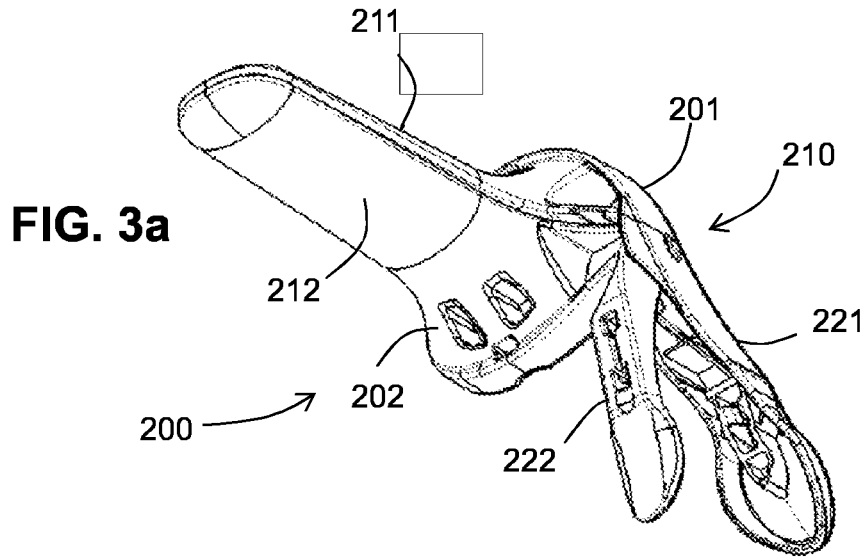
Figure 3B:
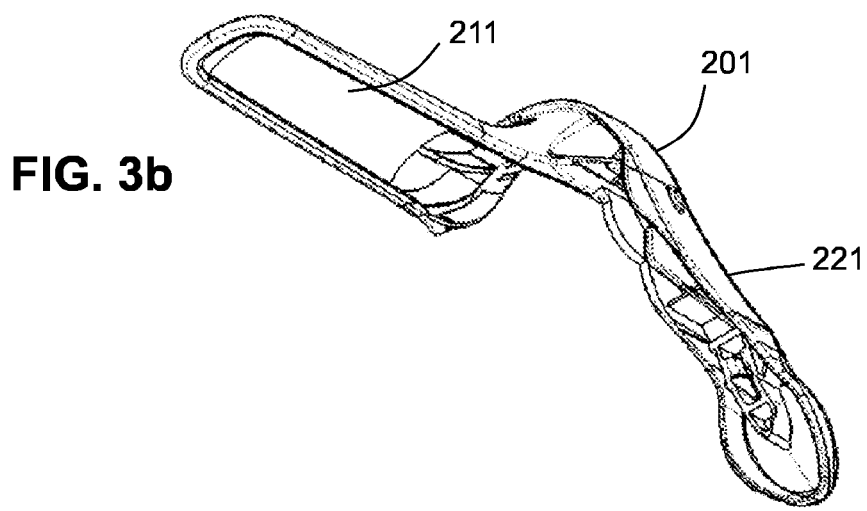
FIG. 3b depicts a view from the second perspective of the first speculum member of FIG. 2b.
Figure 3C:
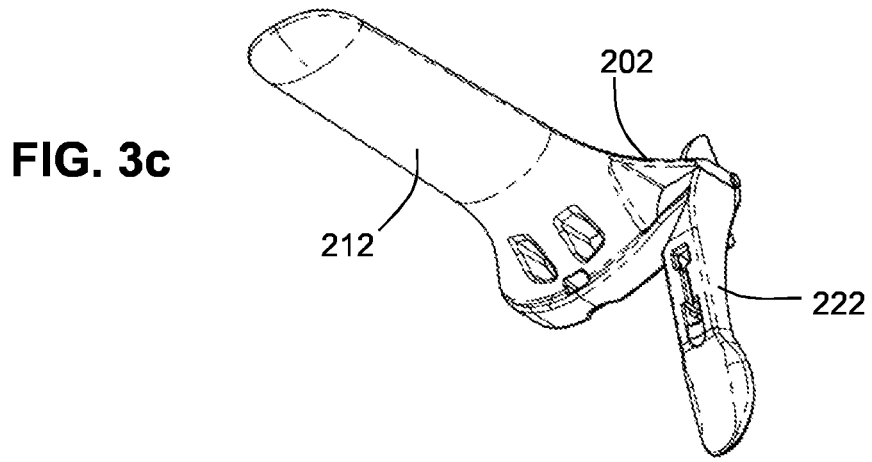
FIG. 3c depicts a view from the second perspective of the second speculum member of FIG. 2c.

FIG. 3a depicts a view from a second, relatively low perspective of the assembled speculum 200. FIG. 3b depicts a view from the second perspective of the first speculum member 201 of the speculum 200. FIG. 3c depicts a view from the second perspective of the second speculum member 202 of the speculum 200.

Figure 4A:
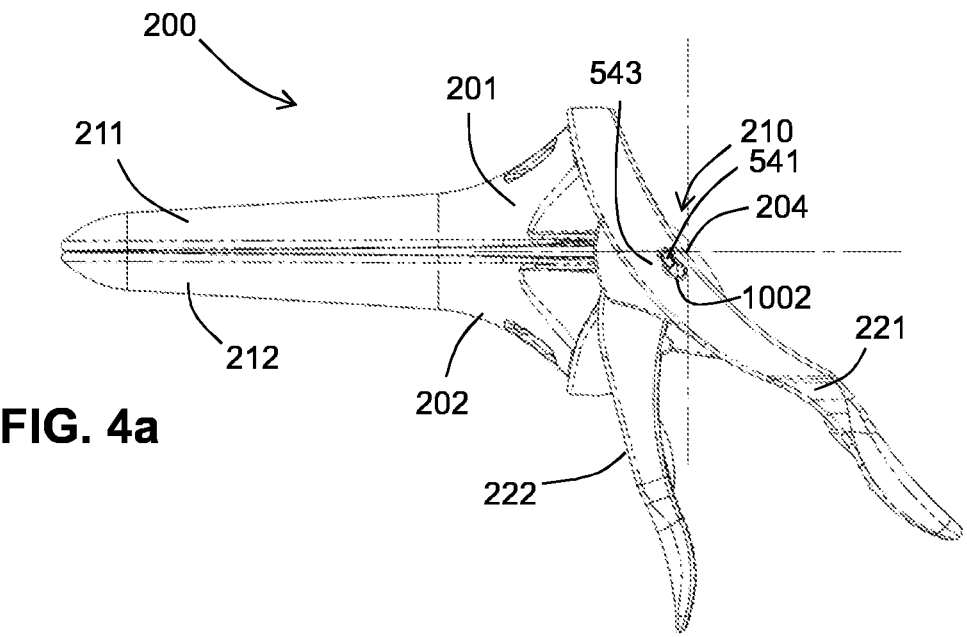
FIG. 4a depicts a side view of the assembled speculum of FIG. 2a, wherein the speculum is in a closed state.

FIG. 4a depicts a side view of the assembled speculum 200, indicating an axis of rotation 204, which can also be referred to as a hinge axis 204. The axis of rotation 204 extends at right angles to the drawing plane of FIG. 4a. The speculum 200 is in a closed state thereof, i.e. the first beak member 211 and the second beak member 212 abut each other along a periphery thereof.

Figure 4B:
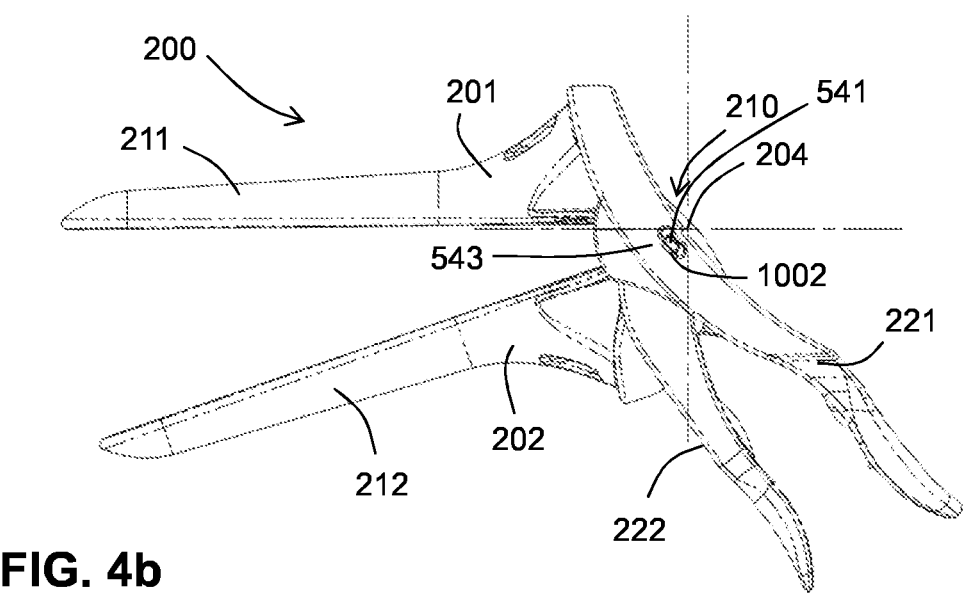
FIG. 4b depicts a side view of the assembled speculum of FIG. 2a, wherein the speculum is in an open state, the first speculum member and the second speculum member being rotated relative to each other around a hinge axis defined by the hinge construction of the speculum.

FIG. 4b depicts a side view of the speculum 200 in an open state thereof, i.e. the first beak member 211 and the second beak member 212 have been rotated relative to each other around the axis of rotation 204 to move the first beak member 211 and the second beak member 212 away from each other, so that the first beak member 211 extends at an acute angle relative to the second beak member 212. The rotating movement of the first beak member 211 and the second beak member 212 relative to each other can also be referred to as a hinging movement, since the rotation is limited to about 30°, whereas FIG. 4b shows a rotation of about 20°.

As can be seen from FIGS. 2a to 4b, the speculum 200 is an open-sided speculum having a hinge construction 210 only at one side of the first speculum member 201 and the second speculum member 202. Accordingly, in use, when bringing the speculum 200 into an open state inside a body cavity of a human or animal body, body tissues are pushed aside by the first beak member 211 and the second beak member 212 moving away from each other by moving the first handle 221 and the second handle 222 towards each other. In this operation of the first handle 221 and the second handle 222, the hinge construction 210 is subjected to axilateral forces, comprising moments exerted on the hinge construction 210 in a plane extending through, or parallel to, the axis of rotation 204, as explained above by reference to FIGS. 1a and 1b, and moments 161 and 162. To absorb such axilateral forces, the hinge construction 210 of the speculum 200 comprises structures as described hereinafter.

Figures 5, 5A:
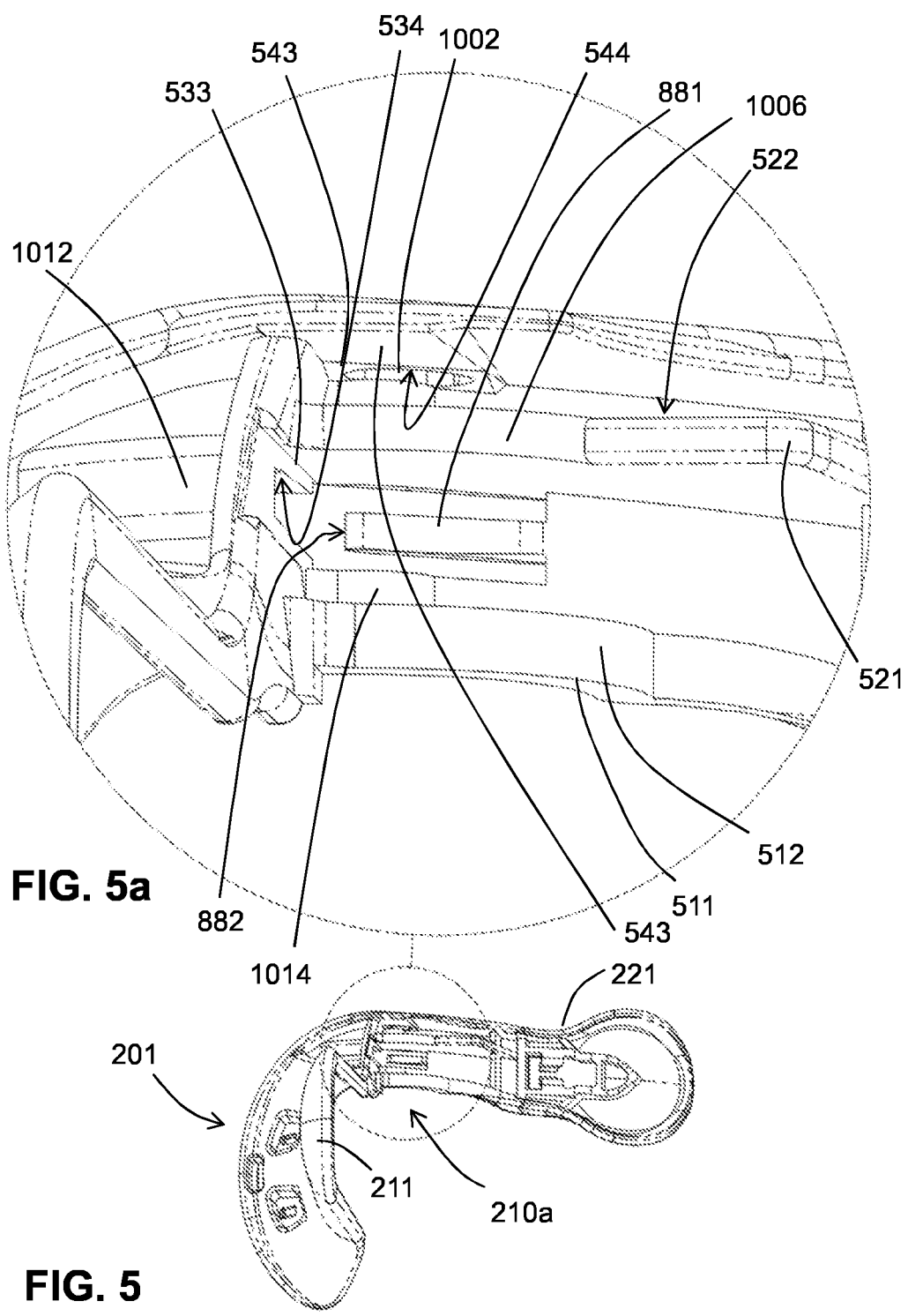
FIG. 5 depicts a view from a third perspective of the first speculum member of FIG. 2b.
FIG. 5a depicts an enlarged view from the third perspective of a portion of the first speculum member of FIG. 2b, showing details of the hinge construction.

FIGS. 5 and 5a depict the first speculum member 201 from a third perspective, showing details of the hinge construction 210.

The first speculum member 201 comprises a first hinge construction part 210a of the hinge construction 210. The first hinge construction part 210a comprises a first support structure 511 having a convex cylinder surface segment shaped first bearing surface 512, which extends in a tangential direction relative to the axis of rotation 204. The first support structure 511 is part of a first bearing structure 510 (see FIG. 7a). The first hinge construction part 210a fixed to the first speculum member 201 further comprises an eighth support structure 543 having, at a side wall of a slot 1002, wherein the side wall is located closest to the first beak member 211, a concave cylinder surface segment shaped eighth bearing surface 544. In FIG. 5a, the eighth bearing surface 544 is located opposite to the partly exposed inner side of the slot 1002. The eighth support structure 543 is part of a fourth bearing structure 540 (see FIG. 7a).

The first hinge construction part 210a further comprises a fin-shaped third support structure 521 having a third bearing surface 522, and a sixth support structure 533, formed by a side wall of a slot, having an sixth bearing surface 534. The third support structure 521 is part of a second bearing structure 520 (see FIG. 9a). The sixth support structure 533 is part of a third bearing structure 530 (see FIG. 7a).

Figure 6A:
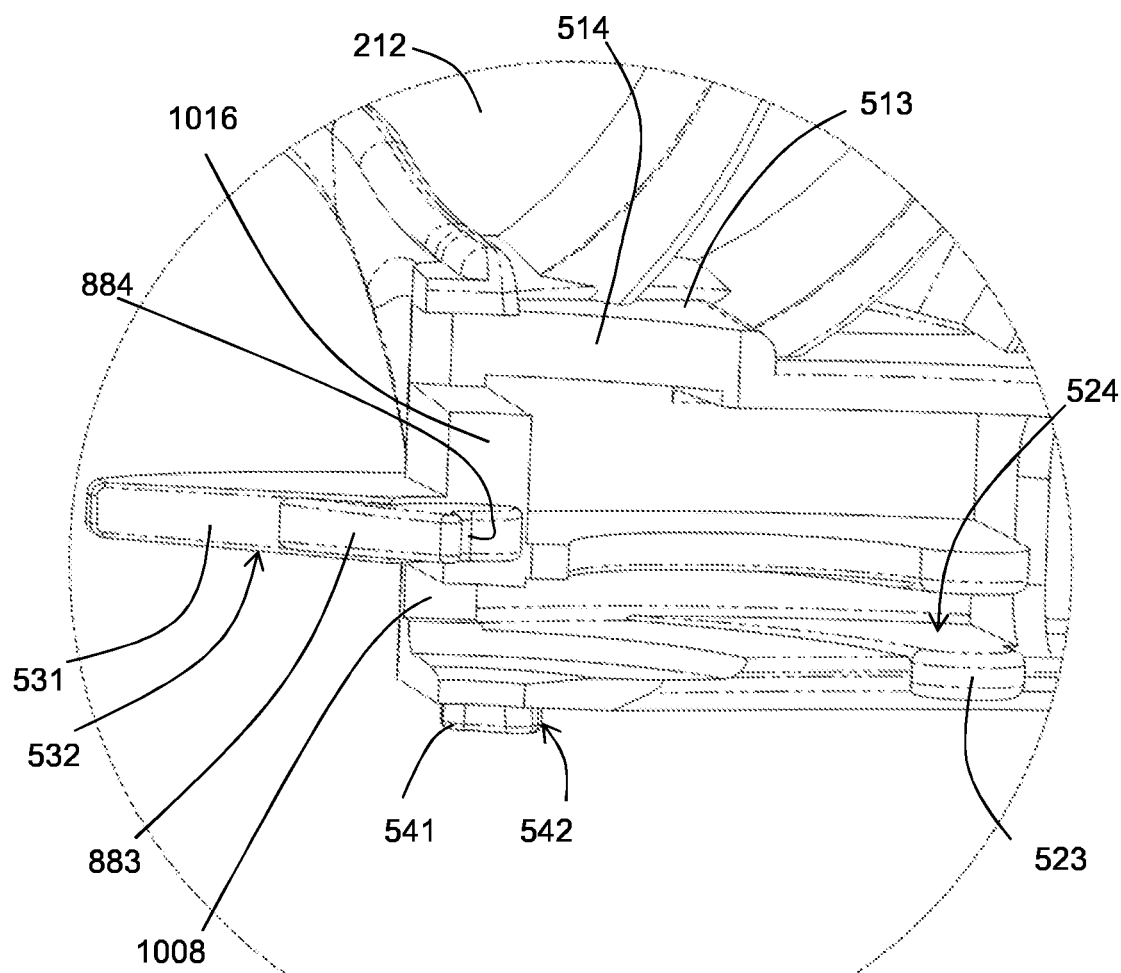
FIG. 6a depicts an enlarged view from the fourth perspective of a portion of the second speculum member of FIG. 2c, showing details of the hinge construction.
Figure 6:
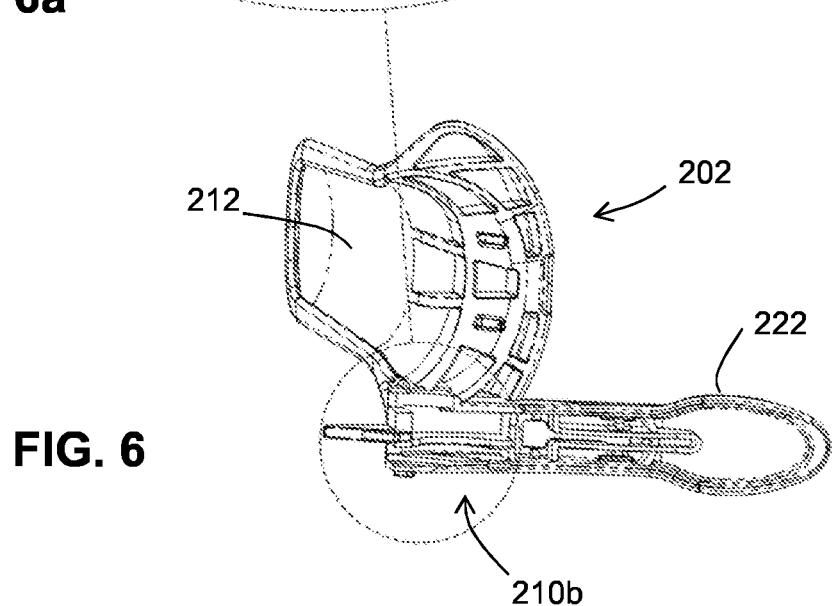
FIG. 6 depicts a view from a fourth perspective of the second speculum member of FIG. 2c.

FIGS. 6 and 6a depict the second speculum member 202 from a fourth perspective, showing details of the hinge construction 210.

The second speculum member 202 comprises a second hinge construction part 210b of the hinge construction 210. The second hinge construction part 210b comprises a second support structure 513 having a concave cylinder segment shaped second bearing surface 514 extending in a tangential direction relative to the axis of rotation 204. The second support structure 513 is part of the first bearing structure 510 (see FIG. 7a). The second hinge construction part 210b fixed to the second speculum member 202 further comprises a notch-shaped seventh support structure 541 having a convex cylinder surface segment shaped seventh bearing surface 542 extending in a substantially tangential direction relative to the axis of rotation 204. In FIG. 6a, the seventh bearing surface 542 is located opposite to the exposed side of the seventh support structure 541. The seventh support structure 541 is part of the fourth bearing structure 540 (see FIG. 7a).

The second hinge construction part 210b further comprises a fourth support structure 523 having a fourth bearing surface 524, and a fin-shaped fifth support structure 531 having a fifth bearing surface 532 extending substantially at right angles to the axis of rotation 204. The fourth support structure 523 is part of the second bearing structure 520 (see FIG. 9a). The fifth bearing surface 532 is part of the third bearing structure 530 (see FIG. 7a).

Figure 7A:
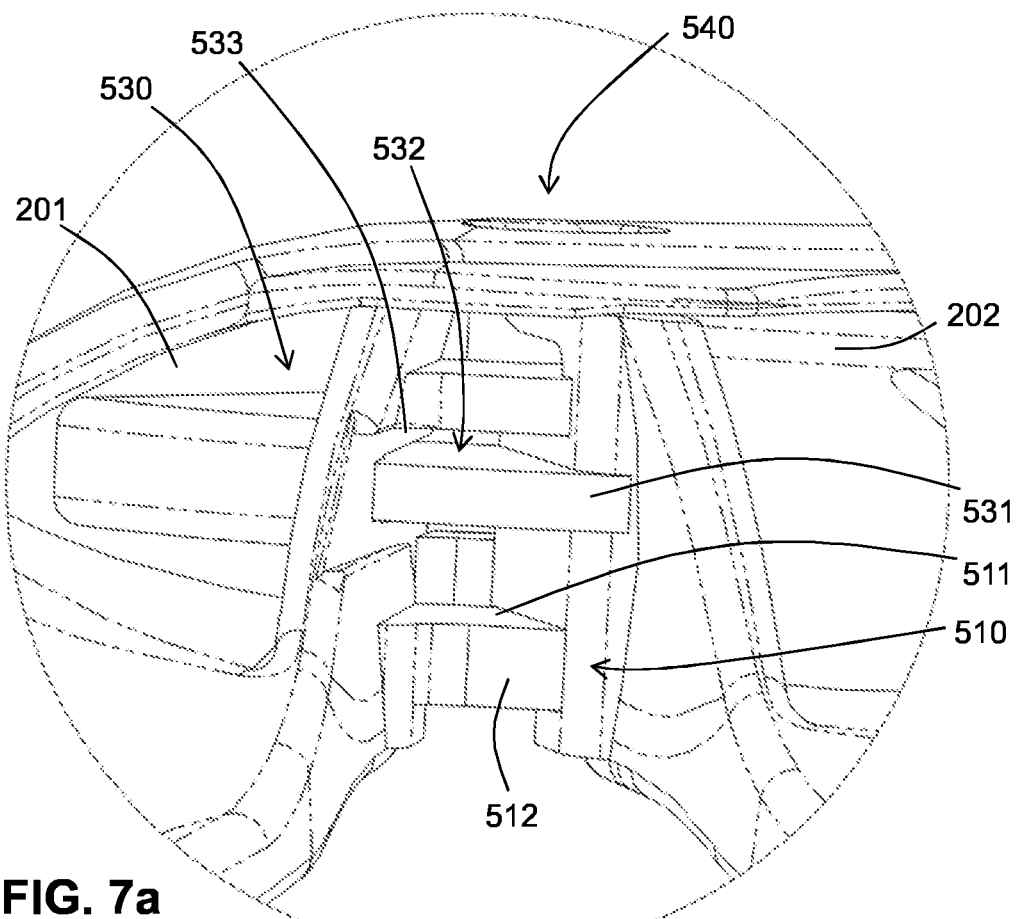
FIG. 7a depicts an enlarged view from the fifth perspective of a portion of the assembled speculum of FIG. 2a, showing details of the hinge construction.
Figure 7:
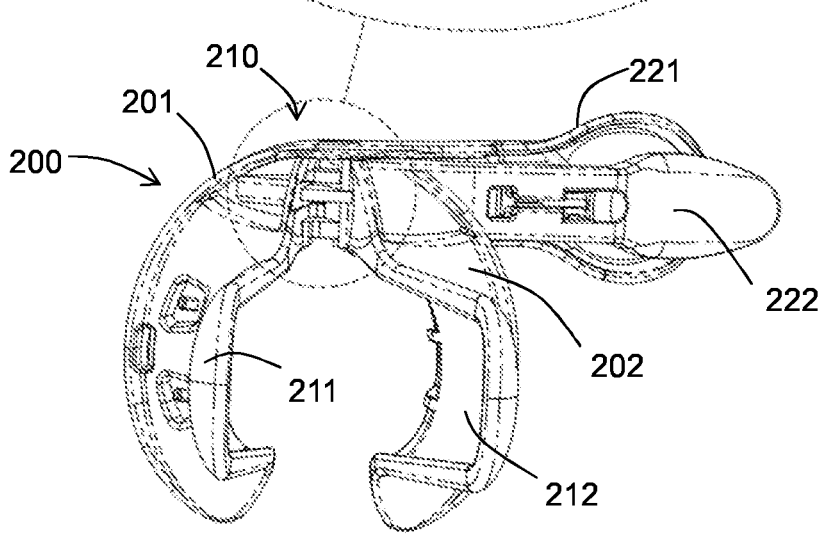
FIG. 7 depicts a view from a fifth perspective of the assembled speculum of FIG. 2a in the open state of FIG. 4b.

The faces of the structures of FIG. 6a appear more clearly from FIGS. 7 and 7a, which depict views from a fifth perspective of the assembled speculum of FIG. 2a in the open state of FIG. 4b, showing details of the hinge construction 210.

Figure 8A:
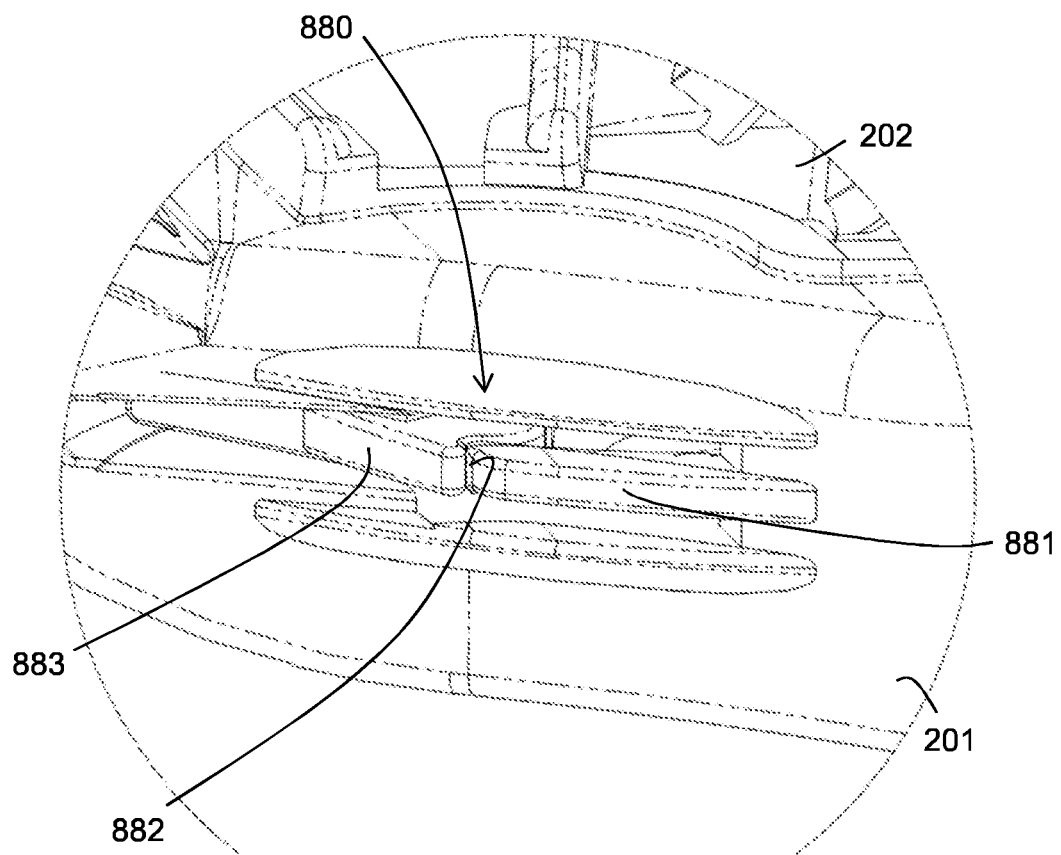
FIG. 8a depicts an enlarged view from the sixth perspective of a portion of the assembled speculum of FIG. 2a, showing details of the hinge construction.
Figure 8:
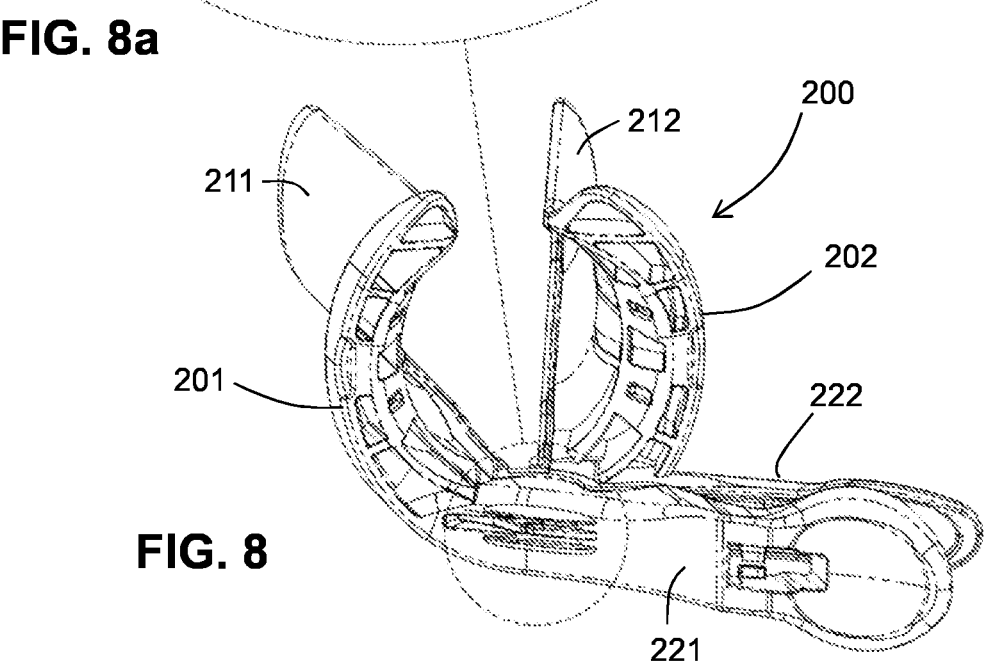
FIG. 8 depicts a view from a sixth perspective of the assembled speculum of FIG. 2a in the open state of FIG. 4b.

FIGS. 8 and 8a depict views from a sixth perspective of the assembled speculum 200 of FIG. 2a in the open state of FIG. 4b, showing details of the hinge construction 210.

The speculum 200 is provided with a radial locking structure 880 comprising a first locking structure 881 and a second locking structure 883. The first speculum member 201 is provided with the first locking structure 881 embodied as an elongate, pin-like, protrusion, having a first locking surface 882. The second speculum member 202 comprises the second locking structure 883, embodied as a hook-like protrusion, having a second locking surface 884. The first locking structure 881 and first locking surface 882 can be better seen in FIG. 5a, whereas the second locking structure 883 and second locking surface 884 can be better viewed in FIG. 6a.

The first locking surface 882 and the second locking surface 884 are configured to maintain mechanical contact during rotation of the first speculum member 201 and the second speculum member 202 relative to each other around the axis of rotation 204, in order to lock the radial positions of the first speculum member 201 and the second speculum member 202 relative to each other while allowing different angular positions thereof relative to each other.

Figure 9A:
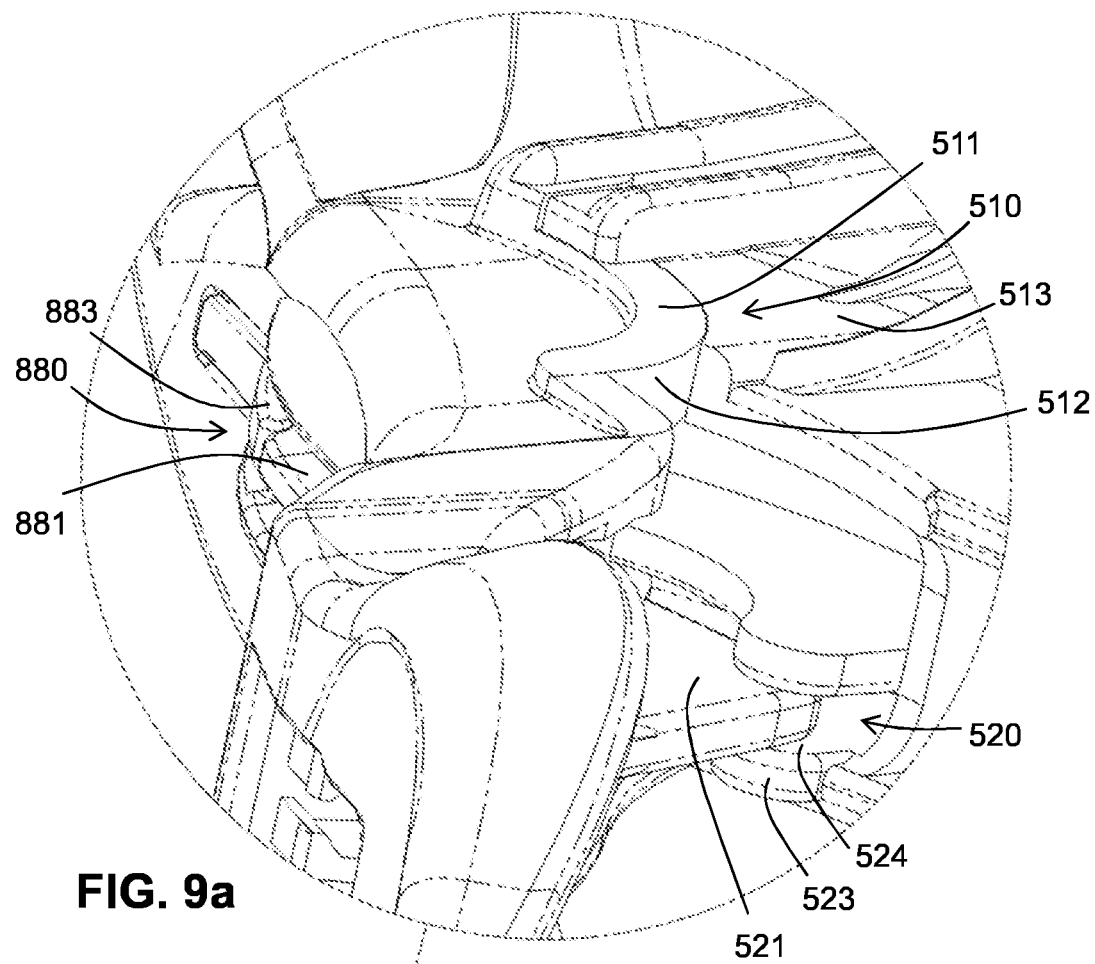
FIG. 9a depicts an enlarged view from the seventh perspective of a portion of the assembled speculum of FIG. 2a, showing details of the hinge construction.
Figure 9:
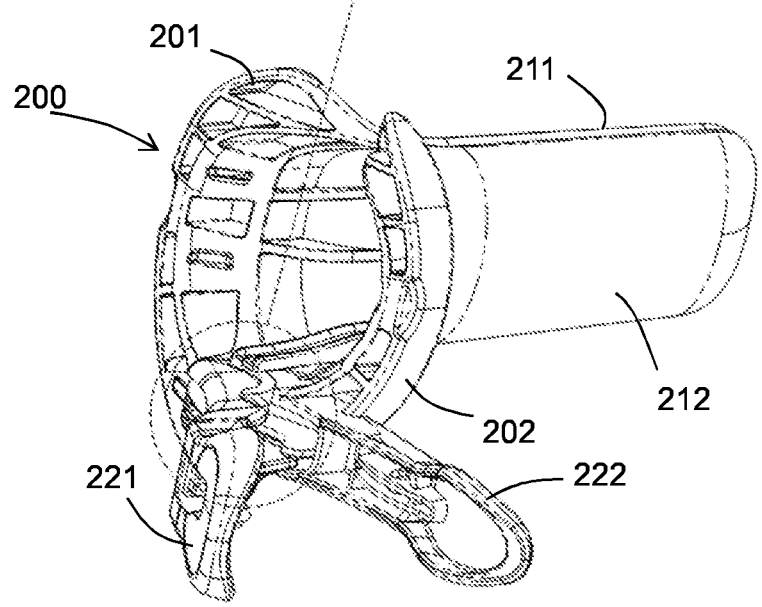

FIGS. 9 and 9a depict views from a seventh perspective of the assembled speculum 200 of FIG. 2a in the closed state of FIG. 4a, showing some details of the hinge construction 210 as explained above, in particular some details of the first bearing structure 510, the second bearing structure 520, and the radial locking structure 880.

Figure 10:
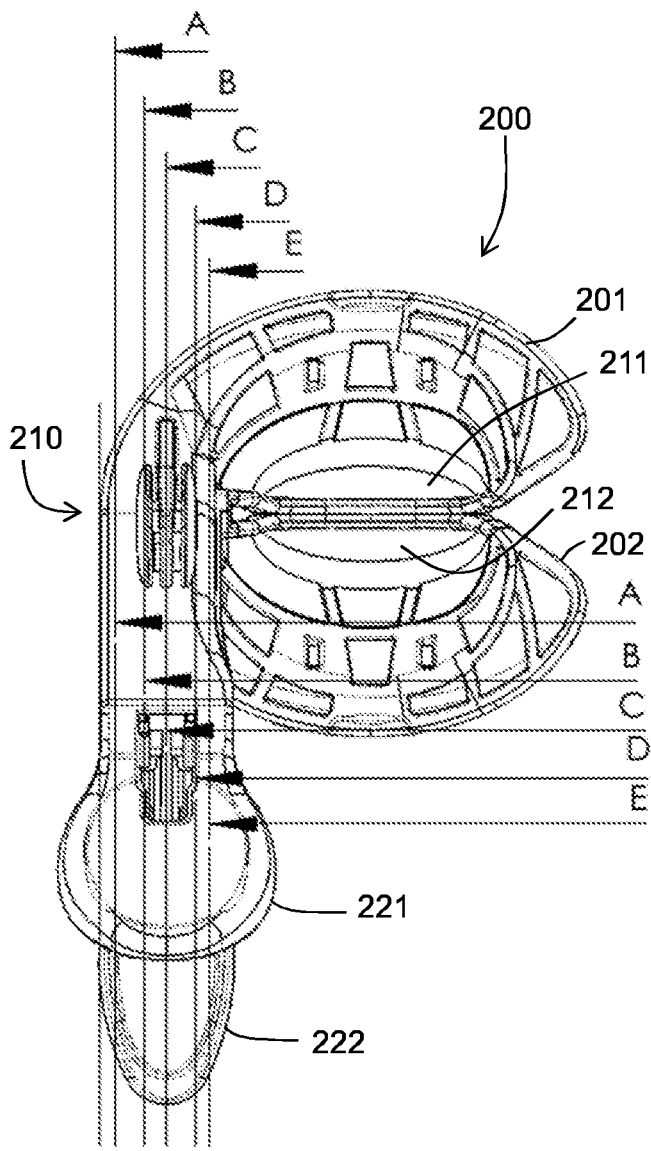

FIG. 10 depicts a back view of the assembled speculum 200 of FIG. 2a in the closed state of FIG. 4a, and FIGS. 10a, 10b, 10c, 10d and 10e depict cross-sectional views taken along lines A-A, B-B, C-C, D-D and E-E, respectively, as shown in FIG. 10, through the hinge construction 210 of the assembled speculum 200 of FIG. 2a.

Figure 10A:
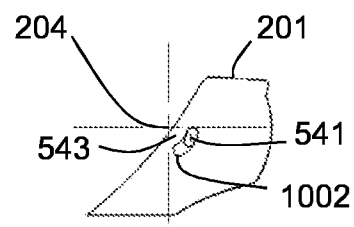

FIG. 10a depicts a part of first speculum member 201 being provided with angular through slot 1002 extending in a tangential direction across a limited angle relative to the axis of rotation 204 of the first speculum member 201 and the second speculum member 202 relative to each other. In the slot 1002, the seventh support structure 541, fixed to the second speculum member 202, is located (see also FIGS. 4a, 4b, and 6a). The seventh support structure 541 is movable in the slot 1002 across a limited angle in a tangential direction around the axis of rotation 204, but is not movable in axial or radial direction relative to the slot 1002.

Figure 10B:

FIG. 10b depicts a part of first speculum member 201 and a part of second speculum member 202, showing the third support structure 521 of the first speculum member 201, where the third bearing surface 522 is located at a side of the third support structure 521 opposite to the side shown in FIG. 10b thereof. As can further be seen in FIG. 10b, a further convex cylinder surface segment shaped bearing surface of a support structure 1006 of the first speculum member 201, the bearing surface extending in a tangential direction relative to the axis of rotation 204, is in mechanical contact with a corresponding concave cylinder surface segment shaped bearing surface of a support structure 1008 of the second speculum member 202.

Figure 10C:
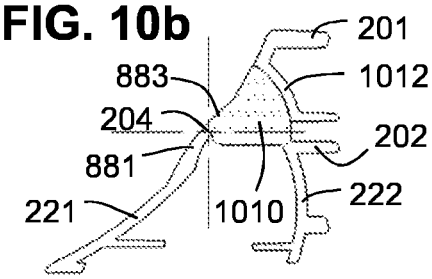

FIG. 10c depicts a part of first speculum member 201 and a part of second speculum member 202, showing the first locking structure 881 and the second locking structure 883 mechanically contacting each other at or near the axis of rotation 204. As can further be seen in FIG. 10c, a further concave cylinder surface segment shaped bearing surface of a support structure 1012 of the first speculum member 201, the bearing surface extending in a tangential direction relative to the axis of rotation 204, is in mechanical contact with a corresponding convex cylinder surface segment shaped bearing surface of a support structure 1010 of the second speculum member 202.

Figure 10D:
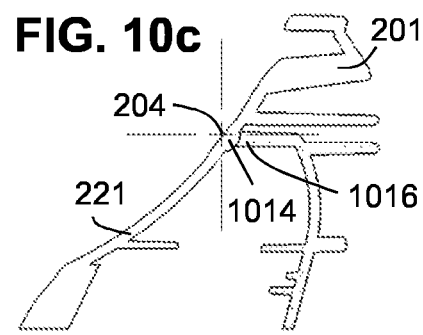

FIG. 10d depicts a part of first speculum member 201 and a part of second speculum member 202, showing a mechanical contact between a further convex cylinder surface segment shaped bearing surface of a support structure 1014 of the first speculum member 201, the bearing surface extending in a tangential direction relative to the axis of rotation 204, and a corresponding concave cylinder surface segment shaped bearing surface of a support structure 1016 of the second speculum member 202.

Figure 10E:
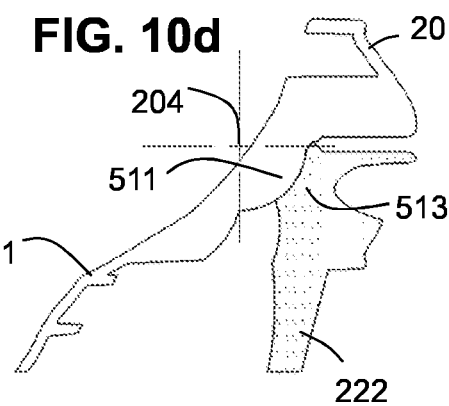

FIG. 10e depicts a part of first speculum member 201 and a part of second speculum member 202, showing the first support structure 511, and the second support structure 513.

FIG. 11 depicts a back view of the assembled speculum 200 of FIG. 2a in the closed state of FIG. 4a, and FIGS. 11a, 11aa, 11b, 11c, 11d, 11 e and 11f depicts cross-sectional views taken along lines F-F, F-F, G-G, H-H, I-I, J-J and K-K, respectively, as shown in FIG. 11, through the hinge construction 210 of the assembled speculum 200 of FIG. 2a.

FIGS. 11a and 11aa depict a part of first speculum member 201 and a part of second speculum member 202, showing the fifth support structure 531, and the sixth support structure 533. As can be seen in particular in FIG. 11aa, a mechanical contact between the fifth support structure 531 and the sixth support structure 533 only exists at a ring segment shaped area between fifth bearing surface 532 and sixth bearing surface 534.

FIGS. 11b and 11c depict a part of first speculum member 201 and a part of second speculum member 202, showing the support structure 1010 of second speculum member 202.

FIGS. 11d and 11e depict a part of first speculum member 201 and a part of second speculum member 202, showing the first support structure 511 of the first speculum member 201, and the second support structure 513 of the second speculum member 202.

Furthermore, the slot 1002 in the first speculum member 201 and the seventh support structure 541 of the second speculum member 202 are shown.

FIG. 11f depicts a part of first speculum member 201 and a part of second speculum member 202, showing third support structure 521 of first speculum member 201, and fourth support structure 523 of second speculum member 202.

As explained in more detail above, a hinge construction hingably connects a first member and a second member which are rotatable about an axis of rotation having an axial direction. The first member and the second member may be part of a surgical instrument, such as a speculum. A first bearing structure comprises first and second support structures having cylinder surface segment shaped first and second bearing surfaces at a radial distance from the axis of rotation, and configured to slidingly engage each other. Second and third bearing structures comprise third, fourth, fifth and sixth support structures having third, fourth, fifth and sixth bearing surfaces, the third and fourth bearing surfaces, and the fifth and sixth bearing surfaces configured to slidingly engage each other to absorb a force having a force component in the axial direction. A fourth bearing structure comprises seventh and eighth support structures having cylinder surface segment shaped seventh and eighth bearing surfaces at a radial distance from the axis of rotation, and configured to slidingly engage each other.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly.

The invention claimed is:

1. A hinge construction for hingably connecting a first member to a second member, wherein the first member and the second member are rotatable relative to each other about an axis of rotation having an axial direction, the hinge construction comprising:
    a first bearing structure comprising a first support structure having a cylinder surface segment shaped first bearing surface at a radial distance from the axis of rotation, and a second support structure having a cylinder surface segment shaped second bearing surface at a radial distance from the axis of rotation, and configured to slidingly engage the first bearing surface, wherein the first support structure is fixed to the first member and the second support structure is fixed to the second member;
    a second bearing structure comprising a third support structure having a third bearing surface, and a fourth support structure having a fourth bearing surface, wherein the third bearing surface and the fourth bearing surface are configured to slidingly engage each other to absorb a force having a force component in the axial direction, wherein the third support structure is fixed to the first member and the fourth support structure is fixed to the second member; and
    a third bearing structure comprising a fifth support structure having a fifth bearing surface, and a sixth support structure having a sixth bearing surface, wherein the fifth bearing surface and the sixth bearing surface are configured to slidingly engage each other to absorb a force having a force component in the axial direction, wherein the fifth support structure is fixed to the second member and the sixth support structure is fixed to the first member.

2. The hinge construction according to claim 1, further comprising:
    a fourth bearing structure comprising a seventh support structure having a cylinder surface segment shaped seventh bearing surface at a radial distance from the axis of rotation, and an eighth support structure having a cylinder surface segment shaped eighth bearing surface at a radial distance from the axis of rotation, and configured to slidingly engage the seventh bearing surface, wherein the seventh support structure is fixed to the second member and the eighth support structure is fixed to the first member.

3. The hinge construction according to claim 2, wherein: one of the seventh and eighth bearing surfaces is convex, and the other one of the seventh and eighth bearing surfaces is concave.

4. The hinge construction according to claim 2, wherein the first and seventh bearing surfaces are convex, and wherein the second and eighth bearing surfaces are concave.

5. The hinge construction according to claim 2, wherein the seventh and eighth bearing surfaces have a second radius with respect to said axis of rotation, and wherein the third and fourth bearing surfaces and/or the fifth and sixth bearing surfaces are positioned away from the axis of rotation at a distance greater than the second radius.

6. The hinge construction according to claim 2, wherein the first bearing surface and the eighth bearing surface, in their tangential direction as seen from the axial direction, at most partly overlap.

7. The hinge construction according to claim 2, wherein the second bearing surface and the seventh bearing surface, in their tangential direction as seen from the axial direction, at most partly overlap.

8. The hinge construction according to claim 2, wherein the first and fourth bearing structures are spaced in the axial direction.

9. The hinge construction according to claim 2, wherein the first, second, third and fourth bearing structures are spaced in the axial direction.

10. The hinge construction according to claim 2, wherein the second and third bearing structures axially are located between the first and fourth bearing structures.

11. The hinge construction according to claim 2, wherein, as seen in the axial direction, the bearing structures are arranged in a sequence of first bearing structure, third bearing structure, second bearing structure, and fourth bearing structure.

12. The hinge construction according to claim 1, wherein: one of the first and second bearing surfaces is convex, and the other one of the first and second bearing surfaces is concave.

13. The hinge construction according to claim 1, wherein at least one of the third, fourth, fifth and sixth bearing surfaces is smooth.

14. The hinge construction according to claim 13, wherein at least one of the third, fourth, fifth and sixth bearing surfaces is ring segment shaped.

15. The hinge construction according to claim 1, wherein at least one of the third, fourth, fifth and sixth bearing surfaces extends substantially at right angles to the axial direction.

16. The hinge construction according to claim 1, wherein the first and second bearing surfaces have a first radius with respect to said axis of rotation, and wherein the third and fourth bearing surfaces and/or the fifth and sixth bearing surfaces are positioned away from the axis of rotation at a distance greater than the first radius.

17. The hinge construction according to claim 1, wherein the third bearing surface and the fifth bearing surface face in the same axial direction.

18. The hinge construction according to claim 1, wherein the third bearing surface and the sixth bearing surface, in their tangential direction as seen from the axial direction, at most partly overlap.

19. The hinge construction according to claim 18, wherein a sum of an angular extension of the third bearing surface and an angular extension of the sixth bearing surface is lower than 180°.

20. The hinge construction according to claim 1, wherein the fourth bearing surface and the fifth bearing surface, in their tangential direction as seen from the axial direction, at most partly overlap.

21. The hinge construction according to claim 20, wherein a sum of an angular extension of the fourth bearing surface and an angular extension of the fifth bearing surface is lower than 180°.

22. The hinge construction according to claim 1, wherein:
one of the third support structure and the fourth support structure is substantially fin-shaped, and/or
one of the fifth support structure and the sixth support structure is substantially fin-shaped.

23. The hinge construction according to claim 1, further comprising a radial locking structure, wherein the radial locking structure comprises:

a first locking structure fixed to the first member, the first locking structure comprising a first locking surface facing in a radial direction with respect to the axis of rotation; and
a second locking structure fixed to the second member, the second locking structure comprising a second locking surface configured to engage the first locking surface.

24. A speculum comprising the hinge construction of claim 1, wherein the first member comprises a first beak member and a first handle securely connected to the first beak member, and wherein the second member comprises a second beak member and a second handle securely connected to the second beak member.

25. The speculum according to claim 24, wherein the hinge construction extends over a first length section of the axis of rotation, and wherein the first beak member and second beak member extend over a second length section of the axis of rotation, wherein the first length section is adjacent the second length section.

26. The speculum according to claim 25, wherein the first handle and the second handle generally extend from the speculum in the first length section of the axis of rotation.

\* \* \* \* \*